ary Examiner — Robert Peshock
United States Patent

Sneer

[11] 3,955,280
[45] May 11, 1976

[54] DENTAL IMPLANTS

[76] Inventor: Meer Sneer, 24 Baalei Melacha St., Tel Aviv, Israel

[22] Filed: Oct. 17, 1973

[21] Appl. No.: 407,244

[30] Foreign Application Priority Data
Oct. 18, 1972 Israel .................................... 40611
Aug. 31, 1973 Israel .................................... 43125

[52] U.S. Cl. ........................................ 32/10 A
[51] Int. Cl.² ...................................... A61C 13/00
[58] Field of Search ............................ 32/10 A

[56] References Cited
UNITED STATES PATENTS

| | | | |
|---|---|---|---|
| 448,745 | 3/1891 | Wright | 32/10 A |
| 2,210,424 | 8/1940 | Morrison | 32/10 A |
| 3,618,212 | 11/1971 | Weissman | 32/10 A |
| 3,790,507 | 2/1974 | Hodosh | 32/10 A |
| 3,797,113 | 3/1974 | Branin | 32/10 A |
| 3,808,606 | 5/1974 | Tronzo | 32/10 A |
| 3,827,145 | 8/1974 | Richards | 32/10 A |
| 3,863,344 | 2/1975 | Pillet | 32/10 A |

FOREIGN PATENTS OR APPLICATIONS

| | | | |
|---|---|---|---|
| 610,723 | 10/1960 | Italy | 32/10 A |
| 540,713 | 3/1956 | Italy | 32/10 A |

Primary Examiner—Robert Peshock
Attorney, Agent, or Firm—Browdy and Neimark

[57] ABSTRACT

An endosseous dental implant comprises in combination a conical foundation member to be inserted into an alveole of the jaw bone or into a hole bored therein. The foundation member has a longitudinal bore open at top and having an interior saw thread at its upper part. A second member adapted to carry an artificial dental element and having a threaded shank is inserted and screwed into the bore of the conical member. Shock absorbing means are provided at the interface of the two elements.

6 Claims, 25 Drawing Figures

Fig. 1

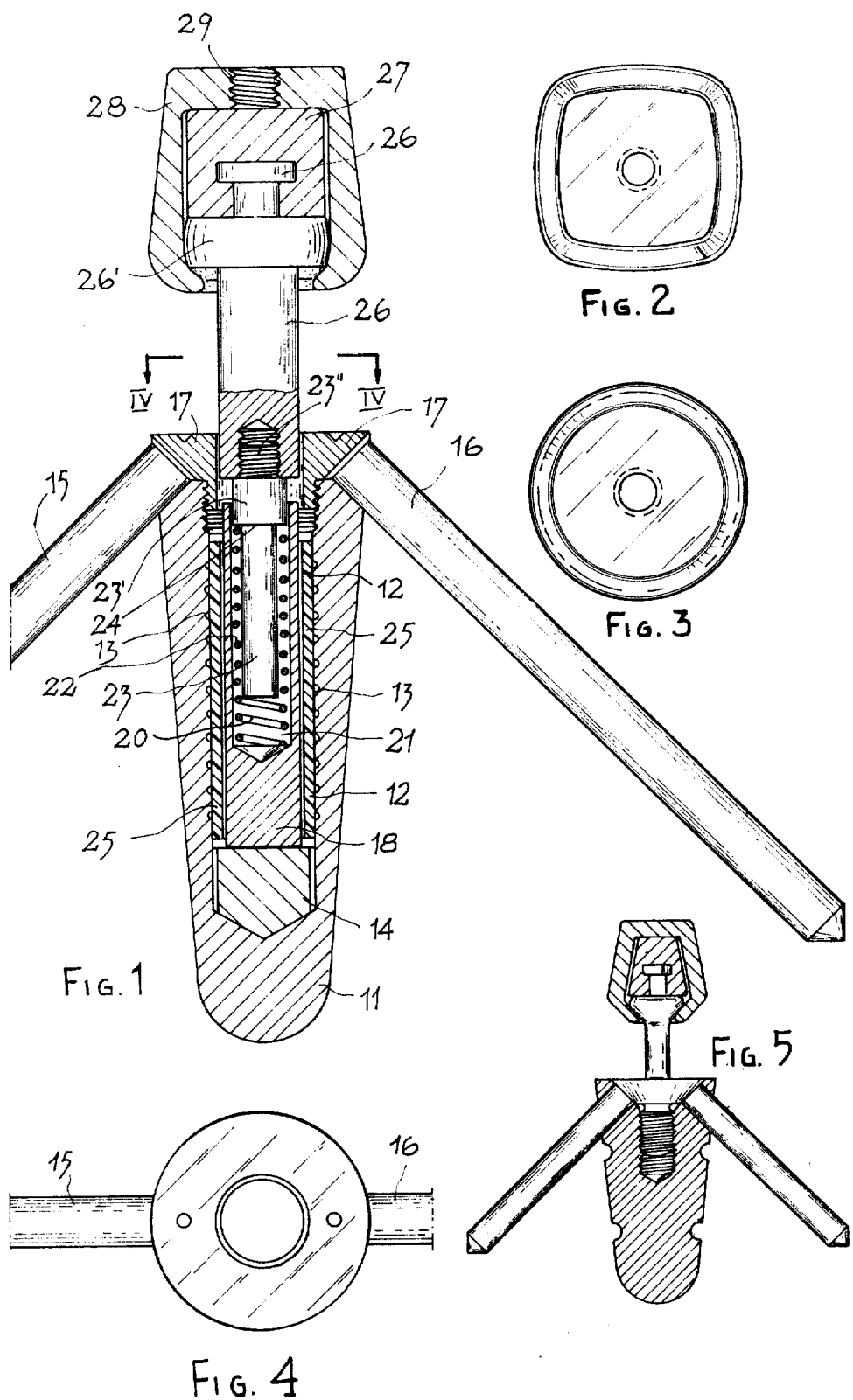

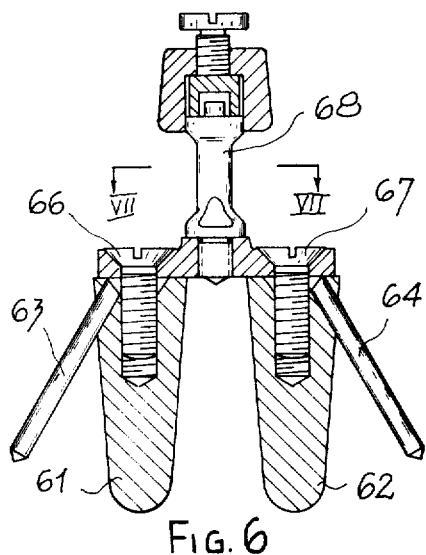
FIG. 6
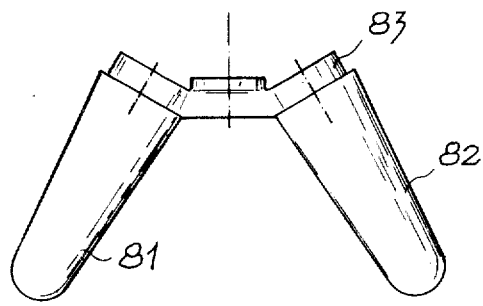
FIG. 8
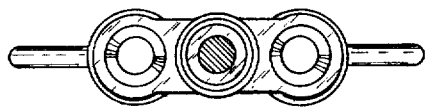
FIG. 7
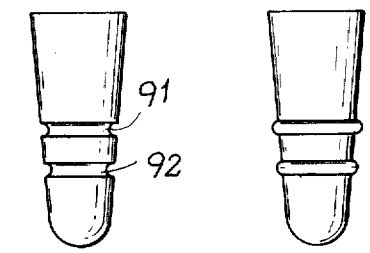
FIG. 9    FIG. 10
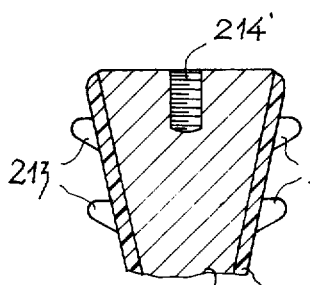
FIG. 14    FIG. 12
FIG. 13
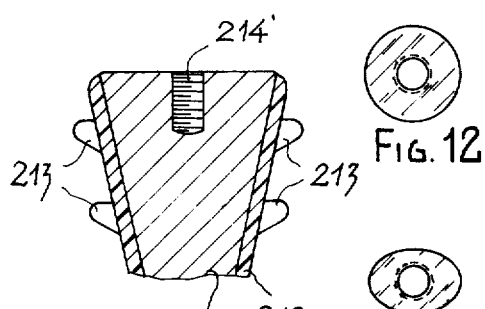
FIG. 15    FIG. 11
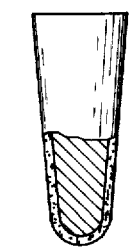
FIG. 19
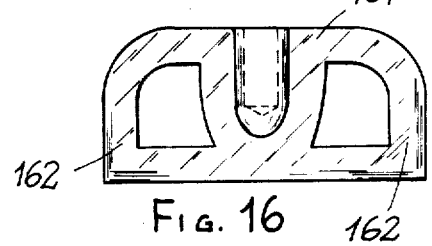
FIG. 16    FIG. 18
FIG. 17

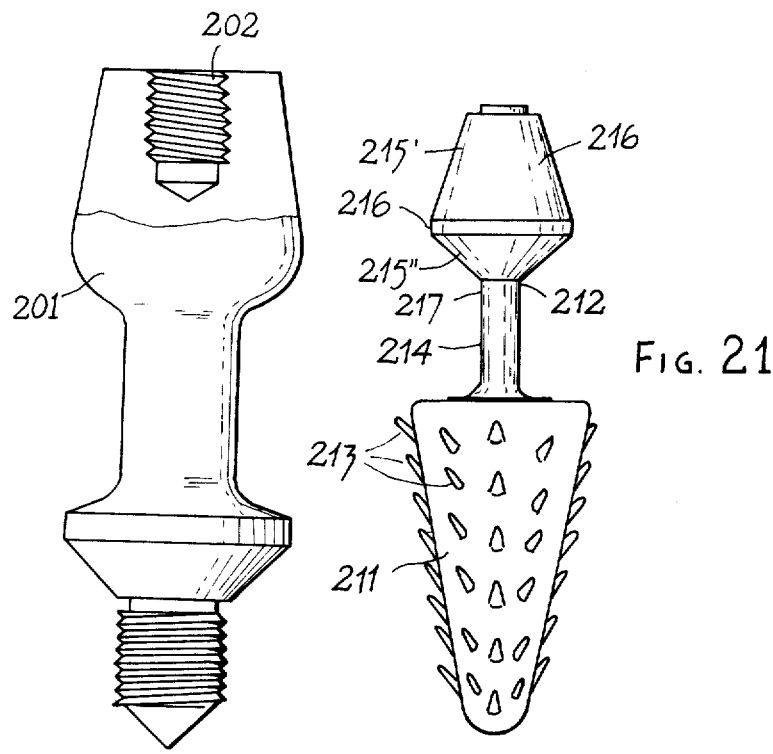
FIG. 20
FIG. 21
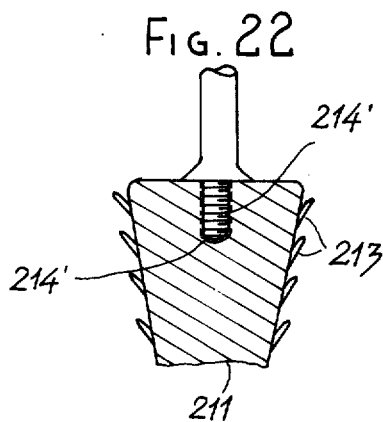
FIG. 22
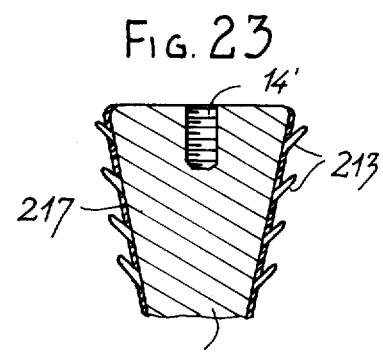
FIG. 23
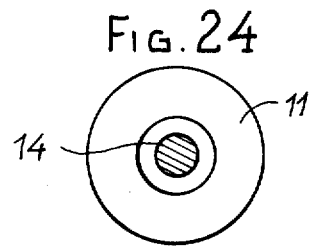
FIG. 24
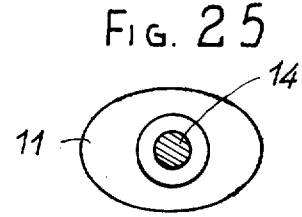
FIG. 25

DENTAL IMPLANTS

BACKGROUND OF INVENTION

The present invention relates to certain improved dental implants. More particularly, it relates to novel constructions for individual intra-osseous tooth implants.

The field of dental implants presents considerable difficulties since frequently infections occur. Therefore it is one of the objects of the present invention to provide a pure implant and to overcome this drawback of dental implants. The implants according to the present invention are intended as crown supports, and supports for dental bridges and the like.

STATE OF THE PRIOR ART

Since about 1954 experiments have been carried out with plastics and with plates juxtaposed to the bone. These procedures have gradually been abandoned due to the surface bone reaction, and research has been directed towards implants which are known as endobone or enosseous implants. In the odontological field, where an implant for fixing a tooth in position is of great interest, various types of implants have been tried out. There may be mentioned the Lehman arch implant, the Sandhaus crystal implant, the Palfer-Sollier implant which has three screws and a head plate, the Cherchewe spiral-screw implant and the Linkow screw implant, the implant formed by three needles so as to form a triangular group etc. These lead often to serious complications because of the rarefaction of the bone, and more particularly of the mandible and also due to the frequent infections which make it necessary to resort to antibiotic and anti-inflammatory treatments.

OBJECTS OF THE INVENTION

The implant of the present invention overcomes to a large extent the drawbacks of the implants used hitherto, and it avoids to a large extent infections or destruction of the bone tissue. The novel implants are easily inserted into the root-canals and into the cavities remaining after the extraction of teeth, they are firmly anchored in such cavities and serve as effective supports for various dental members, such as crowns, bridges and the like. They prevent the degeneration of the jaw-bone after the extraction of a tooth.

SUMMARY OF THE INVENTION

According to a preferred embodiment of the present invention shock-absorbing means are provided in the implant, thus reducing the stresses on the underlying bone tissue. The effective surface area of the novel implants is comparatively large, and thus the pressure and stresses during chewing are distributed on a comparatively large support area.

The novel dental endosseous implant is characterised by substantial advantages as compared with the hitherto used substantial advantages as compared with the hitherto used devices. One of its main features is the provision of means for cushioning the "shock" to the underlying and surrounding bone due to biting and chewing of hard objects. The stresses are absorbed and spread out preventing too large stresses on the bone. A further feature is the "two-stage implant method" which is preferably, but not imperatively, used with these novel dental implant devices.

According to the preferred method of use, there is first inserted a conical foundation pin which serves as support member for the crown-support; this is closed at its upper end and so as to provide a tight closure and this implant is left in place for a period of time sufficient for tissues to form around the implant; and at the second stage, the crown-support member, with its shock absorber or absorbers and the crown or other dental device is mounted on the support member of the foundation pin. It is, of course, also possible to insert the pin and to mount on it without delay the crown-support member, shock absorber and the dental crown, but much better results are attained when sufficient time is permitted to elapse between the first and second stage of the implant for tissue to form around the implant foundation pin.

Amongst the most important features of the novel dental implants according to this invention, there are to be mentioned the following, either separately or in combination:

a. The dental implant is carried out in two stages;
b. The provision of a large specific area of the conical foundation member serving as base of the implant which is in contact with the bone;
c. The provision of efficient shock absorbing means, adapted to cushion the pressure and stresses set up during chewing of food;
d. The provision of a coating of a suitable porous material on the surface of the conical base member of the inserted inplant, adapted to enable bone and other tissue to grow thereinto and/or to form therewith a strong bond, simulating that of a natural tooth with its environment.
e. The provision of protrusions, such as spikes, on the conical foundation member.

It is clear that the above features are to be used either singly or in combination. The provision of a comparatively large surface area in contact with the natural environment of the tooth is an imperative feature and this is of cardinal importance for the success of such implant.

Calculations have shown that the provision of a cone-shaped base provides such large area and as the pressure on the tooth during eating is passed on to the base, i.e. the surrounding bone, the larger the effective area of the base, the smaller the stress will be upon a unit area.

The porous coating provided on the conical base member of the implant permits tissue to grow into the pores of this layer and thus there is gradually formed a strong bond between the implant and the surrounding tissue. This thin layer may be made of two layers having specific properties, the both being provided with small pores, the inner one being a soft and flexible one, providing shock absorbing features, the outer one being rigid and hard. The dimensions of such poses must be of adequate size to permit the surrounding tissue to grow into same. A suitable size of pores is about 50–100 microns.

For anchoring a dental bridge, an implant comprising a plurality of base-cone inserts may be resorted to. Such an embodiment provides a more secure base for dental bridges and similar devices, and it also has further advantages. Thus, for example, when an implant with two foundation cones is implanted, these may be inserted at a certain angle with the upper surface of the jaw-bone, so as to avoid the vicinity of the nerve at the base of the tooth, which may be "straddled" by said implant device.

In case of adverse reaction, the crown-support and the crown or dental bridge supported thereby may be easily removed, the lower part of the implant may be left in place until healing takes place and after this, the upper structure may be re-attached. The two-stage method of implantation avoid epithelization and its adverse results.

According to a preferred embodiment the novel implant according to the present invention provided of a plurality of small protrusions such as spikes or pyramid-like members on the conical surface of the foundation member of the implant, the spikes forming an angle with the conical surface, so as to firmly anchor the implant in place after its insertion in place. The spikes act as barbs, holding the implant in place, holding the implant firmly in place in the cavity in the bone, such as alveole.

BRIEF DESCRIPTION OF DRAWINGS

The invention will now be described by way of illustration only with reference to the enclosed schematical drawings, in which:

FIG. 1 is a schematical side view, in partial section, of a device according to the present invention;

FIG. 2 is a top view of the upper part of the device of FIG. 1;

FIG. 3 is a top view of an alternative form of the upper part of the device shown in FIG. 1.

FIG. 4 is a view taken along lines IV — IV of FIG. 1;

FIG. 5 is a schematical side view of another defice according to the present invention;

FIG. 6 is a schematical side view, in partial section of yet another device according to the invention;

FIG. 7 is a view along lines VI — VI of FIG. 6;

FIG. 8 is a side view of a variation of the lower member of the device shown in FIG. 6;

FIGS. 9 and 10 are slide views of variations of the lower parts of implant devices according to the present invention;

FIG. 11 is a side view in partial section of a foundation cone according to the invention;

FIGS. 12 and 13 are top views of possible shapes of members shown in FIGS. 9 - 11;

FIG. 14 is a schematical side view of a foundation cone provided with protrusions for holding this member in the alveole.

FIGS. 15, 16 and 17 and 18 are respectively the upper and lower part of an implant device according to the invention, a top view of the lower part of the device and a side view thereof;

FIG. 19 is a side view in partial section of a lower member of a device according to the present invention;

FIG. 20 is a schematic side view in partial section of a crown support member;

FIG. 21 is a side view of an implant according to the invention;

FIG. 22 is a vertical median section of the implant of FIG. 21;

FIG. 23 is a vertical median section of a modified foundation conus according to the invention;

FIG. 24 is a top view of the upper part of the implant of FIG. 21;

FIG. 25 is a top view of a modification of the upper part of the implant of FIG. 21.

DESCRIPTION OF PREFERRED EMBODIMENT

As shown in FIG. 1 the endosseous implant pin 11 comprises a conical member rounded at its bottom for insertion into and attachment in the alveoles of an extracted tooth or in a hole drilled in the mandibular bone. The material of the pin 11 must be of adequate mechanical strength and it must be well tolerated by the tissues in contact therewith. Suitable materials are certain metals such as tantalum, gold, nickel, chromium or any other material coated with a suitable protective coating having the required properties of tissue-tolerance. This foundation pin can be brought into position by application of a suitable force.

The two pins 15 and 16, extending at an angle are driven into the bone and the member 17 is screwed in place retaining these in position. The pin 11 is provided with an internal bore 12 and with an internal spiral groove 13. At the bottom of bore 12 there is provided resilient member 14 in contact with the bottom. On member 14 there rests and extends upwards a pin 18 which fits into the internal bore 12. In pin 18 is provided an axial bore 21 in which is accommodated a spring 22 bearing on the bottom of bore 21. Within the spring 22 extends a pin 23 having a thickened uppermost portion 23', thus forming a downwardly facing shoulder 24 which rests on the upper end of spring 22. The pin 18 is surrounded by a sleeve 25 of elastic material.

The thickened portion 23' of pin 23 has an upwardly extending externally screw threaded portion 23" into which screws a cylindrical post 26 having thickened head 26 from which extends upwardly a button 26". On button 26" is slipped a resilient member 27 which carries the hollow carrier 28 intended to carry a tooth fitted thereon. Member 28 has a tapped hole 29 in its top into which a screw threaded tool can be inserted and fixed in case it should be desired to remove member 28 from its seat.

With the pin 11 in position and immobilised in the bone by struts 15 and 16, and a tooth fitted on carrier 28, the whole assembly will respond elastically when the person into whose jaws the prosthesis has been fitted, chews. Downward pressure on the tooth is cushioned first by the member 27, transferred to pin 26, pin 23 which at shoulder 24 bears onto spring 22, which in turn additionally buffers the downward thrust, but transmits it (if not spent) onto the bottom of bore 21 thus acting on pin 18 which rests on the resilient member 14, acting as an additional buffer. In case that the thrust has not been entirely taken up by the bodies 27, the spring 22 and body 14, the lower end of cylinder 26 will come to rest on the upper end of pin 18 and press it down directly onto body 14, thereby fully absorbing the downward thrust.

The pin 11 is implanted in the bone to such depth that the upper surface of member 17 is slightly below the surface of the tissue or even slightly below the surface of the bone. There is inserted at the top a plug of wax and left in place so that there may form tissues around the implanted pin. It is also possible to screw into the bone the pin 11 with the upper part in place. After some time, when the tissues have formed, the tissue on top of the surface of the lower member is temporarily removed, and there is screwed on, on top of the lower member the crown support member shown in FIG. 1. This serves as a support for a crown, denture or other dental device. It is made of a material having adequate mechanical strength, such as metal or hard plastics. When the crown or artificial tooth will be in place, stresses due to biting or chewing will be partially absorbed and distributed over a large surface due to the conical shape of the foundation pin 12 and due to the shock-absorbing means provided.

The foundation pin is held in place due to its conical shape, which exerts a certain wedging action and due to the two lateral fixation pins 15 and 16. The force which results from chewing is absorbed by a combination of a comparatively large surface area of the conical foundation pin, rounded at its bottom, and by the combination of the various shock absorbing means: the resilient material at the lower inner part of the foundation pin, the provision of the resilient material inside this pin, the spring in the pin and the resilient shock absorbing material inside the crown-support member.

As shown in FIG. 2 the shape advantageously resorted to for the crown support member is one which will retain the crown in place without permitting the same to turn. A possible round variation of such member is illustrated in FIG. 3. As shown in FIG. 4 the cross-section of the foundation pin may be a circular one. In order to save space, this may be of an elliptical cross-section as illustrated in FIG. 13. Furthermore, there may be provided a circular cross-section with some of the material removed on opposite sides thereof, and rounded off to prevent any sharp edges.

The foundation pin may be of a conical shape as shown in FIG. 1, but it may be provided with groves 91, 92, in any desired number, as shown in FIG. 9., and the bone growing into such recesses increases the retention of the implanted pin. As shown in FIG. 10, there may be provided lateral protrusions 101, 102, and these have a similar task as the groves.

As shown in FIG. 6, a twin-support member, comprising two foundation pins 61 and 62, may be resorted to. This is of special value where the foundation pins serve as support for a dental bridge. These are inserted into the bone and afterwards the pins 63 and 64 are driven into the bone. As shown in this Figure, the two pins 61 and 62 are connected by a member 65, which is screwed in place by screws 66 and 67. After healing, the upper part is screwed onto the member 65 and this serves as support member for a crown or dental bridge. In this embodiment the two pins are substantially parallel with each other, but as shown in FIG. 8, they may be at a certain angle with each other. As shown here, the implant comprises foundation pins 81 and 82, which are inserted into the mandibular bone, and these are connected with each other by means of the member 83, which serves as support for a crown- or bridge support as shown in FIG. 6.

As shown in FIG. 16 – 18, the foundation pin may comprise a conical foundation members 161 with two blade-shaped members 162 extending from same. This is driven into the bone, and after healing, the upper crown-support member 162, is inserted by screwing into the screw thread provided in the blade-shaped member. This crown-support member is provided with shock absorbing means 164 provided inside the the upper part thereof, consisting of a suitable material of adequate strength and resiliency. The structure of this upper part is similar to that shown in FIG. 1.

Advantageously the conical foundation member is provided with a firmly adhering outer layer of a porous material, such as porous metal, ceramics or metal with a suitable pore size. Experiments have shown that the pore size must have a minimum size of about 50–100 microns so that the tissue can grow into it and form therewith a very strong and intimate bond.

The formation of the oriented conjunctive tissue is a result of the provision of the porous, non-continuous layer of biologically acceptable substance covering the outer surface of the conical foundation pin, the formation of tissue adhering thereto and the subsequent orientation of the thus formed fibrous tissue due to stresses to which the implant is subjected during use (chewing etc.).

Research carried out by many scientists has established that the normal organism forms a fibrous conjunctive tissue around a dental implant which is permanently introduced and fixed in the jaw bone. This fibrous tissue is gradually formed and the process is complete after a period of some months. This tissue adheres well to the bone, but not so to the materials used, conventionally in dental implants, such as continuous metals, ceramic or plastic materials. This is due to the surface properties of these implants and due to the inability of thus formed conjunctive tissue to sufficiently adhere to such materials.

Due to the chewing movement stresses and torque are set up in the conjunctive tissue formed between the bone and the porous layer of the implant, and this stress results in due course in an orientation of this tissue, resulting in the formation of oriented collagen fibres of periodental membrane, similar to that supporting a natural tooth. The repeated stresses and torque applies to this tissue brings about its orientation and strengthening and this results in the dental being held in place in a manner like the holding in place of natural teeth.

As shown in FIG. 21, the novel implant comprises two main parts:

a. a foundation pin, of conical form, 211;
b. a crown-support member, 212.

The conical foundation pin has a height of about 7–10 mm, the diameter at its upper part is about 3–4.5 mm, and on its surface there is provided a plurality of spikes 213, of about 0.5–1.5 mm length and suitable diameter and shape. These are best formed by casting the entire conical support member from a suitable metal. The metal will be chosen so as to be corrosion resistant in the biological environment where it is used and it will be of suitable mechanical properties. Especially suitable are certain stainless steels, of the type used in surgical instruments and in surgery. Especially suited there are certain cobalt-chromium-tungsten alloys. Other metals may be used as well, which fulfil the above criteria; there may also be used certain ceramic substances and even some special plastic materials. As shown in the drawing, the spikes form an angle with the surface of the conus, and point in the direction of the crown-support member 212. The rigid spikes serve to firmly anchor the conical support member in place and prevent its removal from place after insertion.

As shown in FIG. 23 the outer layer of the conical support member may be made from a porous layer 217 attached to the underlying structure, and in this case the spikes 213 are an integral part of the inner metallic core of this conus.

There may be used any suitable porous material, like porous polymer such as porous Teflon; a porous ceramic as a porous metal which is physiologically acceptable.

The porous coating provided on the base of the implant permits tissue to grow into the pores and thus there is gradually formed a strong bond between the implant and the surrounding tissue. This thin layer may be made of two layers having specific properties, the both being provided with small pores, the inner one being a soft and flexible one, providing shock absorbing features, the outer one being rigid and hard.

The crown-support member 212 comprises a lower neck-portion 214, provided at its lower end with a screw adapted to be screwed into the bore 214', provided in the conical member 211, and with a wider upper section 215. This is advantageously divided into two parts 215' and 215'', between which there is provided a shock-absorber 216 comprising a thin layer (about 0.5–1.00 mm) of silicon rubber or the like, firmly glued to sections 215' and 215''.

This shock absorber is advantageously provided, but is not necessary in all cases of implants.

The cross-section of the crown support member is round, as shown in FIG. 24, or it may be ellipsoid as shown in FIG. 25. At the neck-portion of the crown support there is advantageously provided an indentation 217 which makes it possible to screw the crown support member into the foundation conus by means of a suitable tool.

Although termed "crown-support member" this member may also serve as support for a dental bridge, or two such members, implanted with the respective conical foundation pins, into root-channels of a certain extracted tooth, may serve as support for one crown.

Due to the provision of the spikes or other suitable protrusions on the surface of the conical support member, the use of further means of fixation is obviated. The foundation pin is advantageously driven into the root-canal as soon as possible after the extraction of the tooth, and as this is done with some force, the foundation conus is anchored firmly in place. The upper surface of this foundation pin is slightly below the level of the gums and the opening is advantageously claimed or stitched together, and closed with a suitable ointment, such as an anti-inflammatory and anti-infectious ointment such as cortisomol.

After remaining in place for a period of from 2–4 months, so as to provide adequate time for osteogenesis, the consolidation is advantageously checked radiologically. When the osteogenesis has taken place to a satisfactory degree, the upper part is screwed in place and the crown or other dental fixture can be safely and securely mounted thereon.

There ought to be available a wide sortiment of conical foundation members of varying shape (length, thickness, etc.), and as soon as possible after the extraction of the tooth, such foundation pin is inserted in the alveole thus vacated. In other cases it is possible to form a suitable cavity in the bone and to insert thereinto the conical foundation member.

When a tooth is extracted and nothing is done subsequently, the bone in the vicinity degenerates and this results in serious problems, especially in the lower jaw when a prosthesis is to be fitted. In order to provide a better hold, even surgical procedures are resorted to. This can be overcome by inserting into the alveole soon after the extraction of the tooth a conical foundation member, such as the one described with reference to FIGS. 14 and 21–24. This prevents the degeneration of the bone and afterwards it is possible to fit a dental bridge or a prosthesis which has a much better hold on the jawbone.

As shown in FIG. 14, the conical foundation member 211, made of solid material, is provided with a well adhering porous layer 212. lateral protrusions 213, which form an integral part of the cone 211 are provided, which serve to hold the foundation cone firmly in place after its forcible insertion into the jaw-bone.

I claim:

1. An endosseous dental implant, for use in a two-stage implant method, comprising in combination
    a conical foundation member adapted to be inserted into an alveole and corresponding in shape as closely as possible to said alveole, or into a hole bored into the jaw-bone, and to be held therein in a secure manner,
    said foundation member having a longitudinal bore open at the top thereof provided with a thread at its upper end, said foundation member being provided with an external layer of a biologically acceptable porous material consisting of pores having a pore size of 60–100 microns and a plurality of lateral protrusions adapted for firmly and rigidly engaging the surrounding bone to anchor the foundation member therein, and
    a second member adapted to carry an artificial dental element at one of its ends, the other end being provided with a threaded shank adapted to be threaded into the bore of the conical foundation member, and
    effective shock-absorbing means being provided on top of said second member for cushioning stresses during the chewing of food.

2. A dental implant according to claim 1, wherein said shock-absorbing means comprises a cap of resilient material provided at the upper end of the said second member.

3. A dental implant according to claim 1, wherein the foundation member comprises a solid core provided with said external porous material being in the form of surface layer over said solid core.

4. A dental implant according to claim 1, comprising two conical foundation members connected at their upper end with a bridging member.

5. A dental implant according to claim 1, further comprising additional shock-absorbing means for the cushioning of stresses during the chewing of foods, said further effective shock-absorbing means being located within said foundation member.

6. A process for the implantation of a dental impant as claimed in claim 1, which comprises
    first implanting the foundation member,
    leaving it in its place until osteogenesis has taken place to anchor said foundation member firmly in place and form an entity with the surrounding bone, and
    after this inserting the said second member and dental element.

* * * * *